United States Patent
Jiang et al.

(10) Patent No.: US 6,891,017 B2
(45) Date of Patent: May 10, 2005

(54) FAST POLYMERIZABLE/CURABLE EPISULFIDE BASED COMPOSITION, POLYMERIZATION/CURING PROCESS AND OPTICAL ARTICLES RESULTING THEREFROM

(75) Inventors: Peiqi Jiang, Palm Harbor, FL (US); Fadi O. Adileh, Tampa, FL (US); Yassin Yusef Turshani, Largo, FL (US)

(73) Assignee: Essilor International Compagnie General D'Optique, Charenton Cedex (FR)

( * ) Notice: Subject to any disclaimer, the term of this patent is extended or adjusted under 35 U.S.C. 154(b) by 199 days.

(21) Appl. No.: 09/895,446

(22) Filed: Jun. 29, 2001

(65) Prior Publication Data

US 2003/0100641 A1 May 29, 2003

(51) Int. Cl.$^7$ .................. C08G 18/18; C08G 75/00; C08G 75/14
(52) U.S. Cl. .................. 528/379; 528/57; 528/380; 528/390
(58) Field of Search .................. 528/379, 380, 528/390, 57

(56) References Cited

U.S. PATENT DOCUMENTS

| 5,807,975 | A | | 9/1998 | Amagai et al. | .............. 528/373 |
| 5,973,098 | A | * | 10/1999 | Keita et al. | ................... 528/65 |
| 6,130,307 | A | * | 10/2000 | Amagai et al. | ............... 528/73 |

FOREIGN PATENT DOCUMENTS

| EP | 0761665 | 3/1997 |
| EP | 0785194 | 7/1997 |
| EP | 0 942 027 | 9/1999 |
| EP | 1 006 374 | 6/2000 |
| WO | WO 00 26272 | 5/2000 |

OTHER PUBLICATIONS

Co-pending U.S. Appl. No. 09/748,653, filed Dec. 22, 2000.

* cited by examiner

*Primary Examiner*—Tae H. Yoon
(74) *Attorney, Agent, or Firm*—Fulbright & Jaworski L.L.P.

(57) ABSTRACT

The present invention relates to room temperature or thermally polymerizable/curable episulfide based compositions for making polymerized/cured episulfide based resins, and in particular episulfide based compositions which can be fastly polymerized/cured, as well as to a room temperature or thermal polymerization process for making such episulfide based resins.

30 Claims, No Drawings

FAST POLYMERIZABLE/CURABLE EPISULFIDE BASED COMPOSITION, POLYMERIZATION/CURING PROCESS AND OPTICAL ARTICLES RESULTING THEREFROM

BACKGROUND OF THE INVENTION (1) Field of the Invention

The present invention relates to room temperature or thermally polymerizable/curable episulfide based compositions for making polymerized/cured episulfide based resins, and in particular episulfide based compositions which can be fastly polymerized/cured, as well as to a room temperature or thermal polymerization process for making such episulfide based resins.

The polymerizable compositions and the polymerization process of the invention are particularly useful for making optical articles such as lenses, prisms, optical fibers, filters or for making different types of substrates, such as information recording substrates.

The polymerizable compositions and the polymerization process of the invention are also specifically suited for making various coatings and in particular coatings for optical applications.

(2) Description of the Prior Art

Plastic materials are widely used in the optical field and particularly in the ophthalmic field for their lightness, high impact resistance and tintable capability by immersion in a bath containing an organic dye.

Optically transparent plastic materials having a high refractive index $n_D$=1.6 or even higher have been developped recently which renders it possible to manufacture optical articles such as lenses of lower thickness for an equivalent corrective power (optical power).

A class of such materials is comprised of episulfide based resins.

Document U.S. Pat. No. 5,807,975 discloses thermal polymerization and curing of diepisulfides, in particular for the manufacture of optical materials such as a lens material for spectacles. This thermal polymerization/curing of diepisulfides lasts for several hours, generally about 20 hours.

Episulfide compounds and their polymerization process are disclosed in EP-A-761.665 and EP-A-785.194.

Unfortunately, the polymerization of these polymerizable compositions needs a long thermal cycle, generally between 8 hours to several days in order to obtain fully polymerized articles without striation or strain.

Others have disclosed thermal or room temperature polymerization of episulfide compounds using, as catalyst, a salt of formula:

in which $M^{p+}$ is a cation selected from the group consisting of alkaline metals, alkaline earth metals, transition metals and ammonium groups, $Y^-$ is an anion of an acid fulfilling the condition $0.5 \leq Pka \leq 14$, p is the valency of the cation and n=m×p. A preferred catalyst is KSCN.

Although the polymerization time is very significantly decreased when using such a salt catalyst, there is still a requirement to speed up the polymerization of any kind of episulfides without inducing striation and yellowness or without giving a run-away reaction.

SUMMARY OF THE INVENTION

Thus, the aim of the present invention is to provide polymerizable compositions for making episulfide based resins which are thermally polymerizable or polymerizable at room temperature in a short time, typically in less than 6 hours.

The invention also concerns a polymerization process, in particular a room temperature or thermal polymerization process, for making episulfide based resins which necessitates shorter cure time than the prior art processes.

The invention further concerns optical articles such as lenses made of the episulfide base resins resulting from the polymerization of the polymerizable compositions.

It has now been discovered that, by using an effective amount of a catalyst system comprising at least one salt of a specific class of salts and at least one tertiary amine in polymerizable compositions for making episulfide base resins, it was possible to use very short polymerization cycles, typically less than 6 hours, while still obtaining a polymerized resin which is optically transparent and free of striations and having good mechanical, scratch and heat resistance properties.

According to the present invention, there is provided thermally or room temperature polymerizable compositions for making episulfide base resins comprising:

a) a least one episulfide compound bearing at least one episulfide group and at least one functional group capable of polymerizing with episulfide groups; and b) an effective amount of a polymerization catalyst system comprising:

at least one salt of formula:

wherein $M^{p+}$ is a cation selected from the group consisting of alkaline metals, alkaline earth metals, transitions metals and ammonium groups of formula $NR^+_4$ in which R is an alkyl radical, $Y^-$ is an anion such as the corresponding acid YH has a pKa fulfilling the condition $0.5 \leq pKa \leq 14$ with the proviso than when $M^{p+}$ is an ammonium group, the catalyst system further comprises an electro-donor compound, p is the valency of the cation, n=m×p, and at least one tertiary amine.

DETAILED DESCRIPTION OF THE INVENTION AND PREFERRED EMBODIMENTS

The preferred metallic cation of the salts of the catalyst system according to the invention are $Li^+$, $Na^+$, $K^+$, $Rb^+$, $Mg^{2+}$, $Ca^{2+}$ and $Al^{3+}$. The particularly preferred metallic cations are $Li^+$, $Na^+$ and $K^+$ due to their absence of colour and good solubility in the composition. Transition metals are less preferred because the salts thereof lead to coloured compositions and therefore coloured polymerized resins.

The preferred $NR^+_4$ groups are those in which R is a $C_1$–$C_8$ alkyl radical and more preferably, a methyl, ethyl, propyl, butyl or hexyl radical.

Preferably, $Y^-$ is an anion such as the corresponding acid YH which fulfils the conditions $0.5 \leq pKa \leq 10$ and more preferably $0.5 \leq pKa \leq 8$.

Preferably, the anion $Y^-$ is selected from the group consisting of thiocyanate, carboxylate, thiocarboxylate, acetylacetonate, diketone, acetoacetic ester, malonic ester, cyanoacetic ester, ketonitrile and anions of formula $RS^-$ wherein R is a substituted or non substituted alkyl group or phenyl group.

Preferably, the alkyl group is a $C_1$–$C_6$ alkyl group, such as methyl, ethyl and propyl.

The preferred anions $Y^-$ are $SCN^-$, acetylacetonate, acetate, thioacetate, formate and benzoate.

The most preferred salt is KSCN.

Generally, the salt will be present in amounts ranging, based on the total weight of the polymerizable monomers present in the composition, from 0.001 to 2,5%, preferably 0.001 to 1%.

The tertiary amines of the catalyst system according to the invention may be represented by the formula:

$$(R)_3N \qquad (I)$$

in which the R groups represent, independently from each other, an alkyl radical, generally a $C_1$–$C_6$ alkyl radical such as methyl, ethyl and propyl, preferably methyl, a cycloalkyl radical, generally a $C_5$–$C_{10}$ cycloalkyl radical such as cyclopentyl, cyclohexyl and cycloheptyl, preferably cyclohexyl, or mixtures thereof.

Among the preferred tertiary amines, there may be cited N,N-dimethylcyclohexylamine and N,N-dicyclohexylmethylamine.

Generally, the tertiary amine will be present in amounts ranging, based on the total weight of the polymerizable monomers present in the composition, from 0.5 to 5%, preferably from 0.05 to 2%.

In a preferred embodiment, the catalyst system according to the present invention further includes at least one electro-donor compound. The electro-donor compounds are preferably selected from the group consisting of acetonitrile compounds, amide compounds, sulfones, sulfoxides, trialkylphosphites, triarylphosphites, nitro compounds, ethyleneglycol ethers, crown ethers and kryptates.

Examples of acetonitrile compounds are:

in which R is an alkyl group, preferably a $C_1$–$C_6$ alkyl group such as methyl, ethyl, propyl, butyl.

The amide compounds may be primary, secondary or tertiary amide compounds.

The triakylphosphites and triarylphosphites may be represented by formula:

in which R, R', R''' are either an alkyl group, preferably a $C_1$–$C_6$ alkyl group or an aryl group such as a phenyl group. Preferred are trialkylphosphites, for example $(C_2H_5O)_3P$.

Electro-donor compounds are preferably selected from crown ethers and kryptates.

These cyclic molecules are usually chosen to exhibit a good compromise between the heteroatom or metal size and the "cage" size, i.e. between the number of heteroatoms and the size of the cycle.

The preferred crownethers and kryptates may be represented by the following formulae:

and

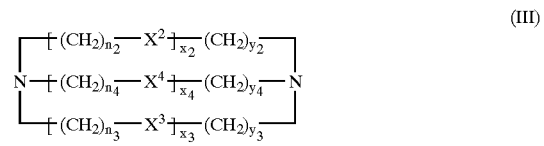

wherein $X^1$ represents O, S or NH, $x_1$ is an integer from 3 to 6, preferably from 3 to 4, $X^2$, $X^3$ and $X^4$ represent O or S, $n_2$, $n_3$, $n_4$, $y_2$, $y_3$, $y_4$ are 2 or 3, and $x_2$, $x_3$, $x_4$ are 2 or 3.

Among the preferred crown ethers and kryptates there may be cited the following compounds:

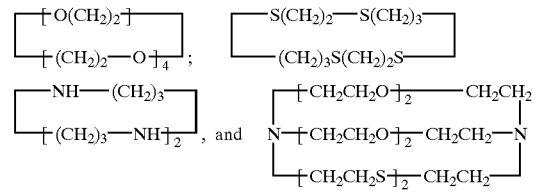

The electro-donor compounds are present, based on the total weight of the polymerizable monomers in amounts ranging from 0 to 5% by weight, preferably 0 to 1% by weight.

Preferred electro-donor compounds are crown-ethers, kryptates, trialkyl phosphites and aceto nitrile compounds, and most preferably crown-ethers such as 18-crown-6, 18-crown-7, 15-crown-5 and 15-crown-6.

The polymerizable compositions of the present invention may comprise a solvent for promoting the dissolution of the salt catalyst within the monomer.

Any polar organic solvent can be used such as acetonitrile, tetrahydrofurane or dioxane. However, to avoid bubble generation, it is preferred to use a reactive solvent containing a hydroxyl function. Suitable solvents are methanol, ethanol, acetone, acetonitrile, 3-methyl-2-butene-1 ol and 2-mercaptoethanol.

The amount of solvent is generally kept below 10% by weight, based on the total weight of the polymerizable monomers present, and is preferably about 5% by weight or less, to avoid haze and bubbling.

The polymerizable episulfide monomers of the invention have at least one episulfide functionality and preferably two or more episulfide functionalities per molecule.

The functional groups capable of polymerising with episulfide groups are epoxy, isocyanate, isothiocyanate, thiols, unsaturated c=c bonds such as acrylic, thioacrylic.

The most preferred episulfide monomers contain solely two episulfide functionalities and no other reactive functionality.

Preferably, the polymerizable monomers having at least one episulfide functionality are compounds having one or more episulfide structures represented by the following formula (IV) in one molecule:

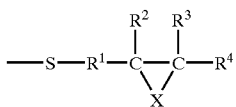
                                                            (IV)

in which $R_1$ represents a hydrocarbon group having 1 to 10 carbon atoms, $R^2$, $R^3$ and $R^4$ each represents an hydrogen atom or a hydrocarbon group having 1 to 10 carbon atoms, X represents S or O with the provisio that in the molecule the average number of S represented by X is about 50% of the total number of S and O constituting the three membered ring.

A preferred class of polymerizable episulfide monomer is represented by compound of formula (V):

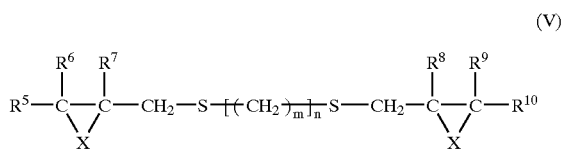
                                                            (V)

in which $R^5$, $R^6$, $R^7$, $R^8$, $R^9$ and $R^{10}$ each represents an hydrogen atom or a hydrocarbon group having 1 to 10 carbon atoms, X represents S or O with the proviso that, in the molecule, the average number of S represented by X is about 50% or more of the total number of S and O constituting the three member rings, m represents an integer from 0 to 6 and n represents an integer from 0 to 4.

Preferably, $R^1$ in formula (IV) represents a methylene group or ethylene group and $R^2$, $R^3$ and $R^4$ in formula (IV) and $R^5$, $R^6$, $R^7$, $R^8$, $R^9$ and $R^{10}$ in formula (V) each preferably represents a hydrogen atom or a methyl group. It is more preferably that $R^1$ represents a methylene group and $R^2$, $R^3$, $R^4$, $R^5$, $R^6$; $R^7$, $R^8$, $R^9$ and $R^{10}$ each represents a hydrogen atom.

The average number of S in each of formula (IV) and formula (V) is 50% or more, preferably 90% or more, more preferably 95% or more and more preferably substantially 100% of the total number of S and O constituting the three member rings.

Examples of these compounds include linear organic compounds such as bis(β-epithiopropylthio)methane, 1,2-bis(β-epithiopropylthio)ethane, 1,3-bis(β-epithiopropylthio)propane, 1,2-bis(β-epithiopropylthio)propane, 1-(β-epithiopropylthio)butane, 1,3-bis(β-epithiopropylthio)butane, 1-(β-epithiopropylthio)-3-(β-epithiopropylthiomethyl)butane, 1,5-bis(β-epithiopropylthio)pentane, 1-(β-epithiopropylthio)-4-(β-epithiopropylthio-methyl)pentane, 1,6-bis(β-epithiopropylthio)hexane, 1-(β-epithiopropylthio)-5-(β-epithiopropylthiomethyl)hexane, 1-(β-epithiopropylthio)-2-[(2-(β-epithiopropylthioethyl)thio]ethane and 1-(βepithiopropylthio)-2-[[2-(2-β-epithiopropylthioethyl)thioethyl]thio]ethane; branched organic compounds such as tetrakis(β-epithiopropylthiomethyl)methane, 1,1,1-tris(β-epithiopropylthiomethyl)propane, 1,5-bis(β-epithiopropylthio)-2-(β-epithiopropylthiomethyl)-3-thiapentane, 1,5-bis(β-epithiopropylthio)-2,4-bis(β-epithiopropylthiomethyl)-3-thiapentane, 1-(β-epithiopropylthio)-2,2-bis(β-epithiopropylthiomethyl)-4-thiahexane, 1,5,6-tris(β-epithiopropylthio)-4-(β-epithiopropylthiomethyl)-3-thiahexane, 1,8-bis(β3-epithiopropylthio)-4-(β-epithiopropylthiomethyl)-3,6-dithiaoctane, 1,8-bis(β-epithiopropylthio)-4,5-bis(β-epithiopropylthiomethyl)-3,6-dithiaoctane, 1,8-bis(β-epithiopropylthio)-4,4-bis(β3-epithiopropylthiomethyl)-3,6-dithiaoctane, 1,8-bis(β-epithiopropylthiomethyl)-2,4,5-tris(β-epithiopropylthiomethyl)-3,6-dithiaoctane, 1,8-bis(β-epithiopropylthio)-2,5-(β-epithiopropylthiomethyl)-3,6-dithiaoctane, 1,9-bis(β-epithiopropylthio)-5-(β-epithiopropylthiomethyl)-5-[(2-β-epithiopropylthioethylthiomethyl]-3-7-dithianonane, 1,10-bis(β-epithiopropylthio)-5,6-bis[2-β-epithiopropylthioethyl)thio]-3,6,9-trithiadecane, 1,11-bis(β-epithiopropylthio)-4,8-bis(β-epithiopropylthiomethyl)-3,6,9-trithiaundecane, 1,11-bis(β-epithiopropylthio)-5,7-bis(β-epithiopropylthiomethyl)-3,6,9-trithiaundecane, 1,11-bis(β-epithiopropylthio)-5,7-[(2-β-epithiopropylthio)thiomethyl]-3,6,9-trithiaundecane and 1,11-bis(β-epithiopropylthio)-4,7-bis(β-epithiopropylthiomethyl)-3,6,9-trithiaundecane; and compounds obtained by substituting at least one hydrogen atom of the episulfide group in the above compounds with methyl group, cyclic aliphatic organic compounds such as 1,3- and 1,4-bis(β-epithiopropylthio)cyclohexanes, 1,3- and 1,4-bis(β-epithiopropylthiomethyl)cyclohexanes, bis[4-(β-epithiopropylthio)cyclohexyl]methane, 2,2-bis[4-(β-epithiopropylthio)cyclohexyl]propane, bis[4-(β-epithiopropylthio)cyclohexyl]sulfide, 2,5-bis(β-epithiopropylthiomethyl)-1,4-dithiane and 2,5-bis(β-epithiopropylthioethylthiomethyl)-1,4-dithiane; and compounds obtained by subtituting at least one hydrogen atom of the episulfide group in the above compounds with methyl group and aromatic organic compounds such as 1,3- and 1,4-bis(β-epithiopropylthio)benzenes, 1,3- and 1,4-bis(β-epithiopropylthiomethyl)benzenes, bis[4-(β-epithiopropylthio)phenyl]methane, 2,2-bis[4-(β-epithiopropylthio)phenyl]propane, bis[4-(β-epithiopropylthio)phenyl]sulfide, bis[4-(β-epithiopropylthio)phenyl]sulfone and 4,4'-bis(β-epithiopropylthio)biphenyl; and compounds obtained by substituting at least one hydrogen atom of the episulfide group in the above compounds with methyl group. However, compound (a) is not limited to the above compounds shown as examples. The above compounds may be used singly or as a mixture of two or more compounds.

The most preferred episulfide compounds are bis(β-epithiopropyl)sulfide of formula:

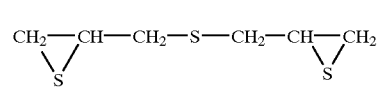
                                                            (VI)

and bis(β-epithiopropyl)disulfide of formula:

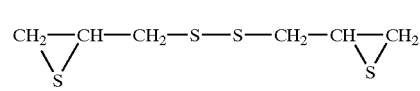
                                                            (VII)

The polymerizable composition of the invention may further include up to 30% by weight, preferably up to 15%, based on the total weight of polymerizable monomers, of one ore more polythiol monomers having two or more, preferably two to four thiol functions.

The polythiol monomers can be represented by formula (VIII):

                                                            (VIII)

in which n' is an integer from 2 to 6, preferably 2 to 4, and R' is an organic group of valency equal to n'.

Useful polythiol monomers are those disclosed in EP-A-394,495 and U.S. Pat. No. 4,775,733 and the polythiols corresponding to the following formulas:

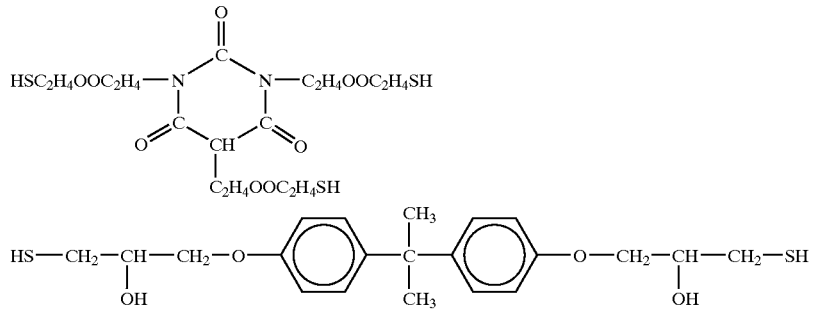

and

Among the preferred polythiol monomers there may be cited aliphatic polythiols such as pentaerythritol tetrakis mercaptoproprionate. 1-(1'-mercaptoethylthio)-2-3-dimercaptopropane, 1-(2'-mercaptopropylthio)-2,3-dimercaptopropane, 1-(3'-mercaptopropylthio)-2,3-dimercaptopropane, 1-(4'-mercaptobutylthio)-2,3-dimercaptopropane, 1-(5'-mercaptopentylthio)-2,3 dimercapto-propane, 1-(6'-mercaptohexylthio)-2,3-dimercaptopropane, 1,2-bis(-4'-mercaptobutylthio)-3-mercaptopropane, 1,2-bis(5'-mercaptopentylthio)-3-mercaptopropane, 1,2-bis(6'-mercaptohexyl)-3-mercaptopropane, 1,2,3-tris(mercaptopropylthio)propane, 1,2,3-tris(3'-mercaptoethylthio)propane, 1,2,3-tris(2'-mercaptoethylthio)propane, 1,2,3-tris(4'-mercaptobutylthio)propane, 1,2,3-tris(6'-mercaptohexylthio)propane, methanedithiol, 1,2-ethanedithiol, 1,1-propanedithiol, 1,2-propanedithiol, 1,3-propanedithiol, 2,2-propanedithiol, 1,6-hexanethiol-1,2,3-propanetrithiol, 1,2-bis(2'-mercaptoethylthio)-3-mercaptopropane, 2-(2-sulfanylethylthio)-3-[3-sulfanyl-2-(2-sulfanylethylthio)propylthio]propane-1-thiol and mixtures thereof.

Preferred polythiol monomers are 1,2-bis(2'-mercaptoethylthio)-3-mercaptopropane and 2-(2-sulfanylethylthio)-3-[3-sulfanyl-2-(2-sulfanylethylthio)propylthio]propane-1-thiol.

The addition of polythiol monomer in the composition of the invention reduces haze and striation and improves smooth polymerization.

The composition of the invention may also include up to 30% by weight, preferably no more than 15%, based on the total weight of polymerizable monomers present in the composition, of one or more polyiso(thio)cyanate, preferably polyisocyanate monomers having two ore more iso(thio)cyanate functions per molecule, preferably two or three iso(thio)cyanate functions.

The preferred polyiso(thio)cyanate monomers are those having the formulae:

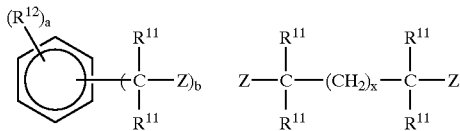

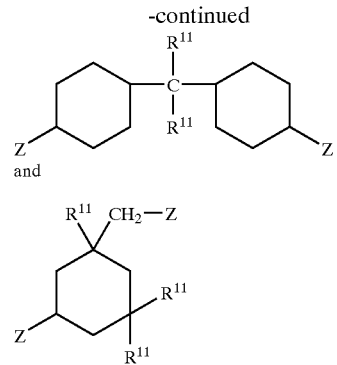

wherein:
$R^{11}$ is independently H or $C_1$–$C_5$ alkyl group, preferably $CH_3$ or $C_2H_5$;
$R^{12}$ is H, an halogen, preferably Cl or Br, or a $C_1$–$C_5$ alkyl group, preferably $CH_3$ or $C_2H_5$;
Z is —N═C═O or —N═C═S, preferably —N═C═O;
a is an integer ranging from 1 to 4, b is an integer ranging from 2 to 4 and a+b≦6; and
x is an integer from 1 to 10, preferably 1 to 6.

Among the preferred polyiso(thio)cyanate monomers there may be cited tolylene diiso(thio)cyanate, phenylene diiso(thio)cyanate, ethylphenylene diiso(thio)cyanate, isopropyl phenylene diiso(thio)cyanate, dimethylphenylene diiso(thio)cyanate, diethylphenylene diiso(thio)cyanate, diisopropylphenylene diiso(thio)cyanate, trimethylbenzyl triiso(thio)cyanate, xylylene diiso(thio)cyanate, benzyl triiso(thio)cyanate, 4,4'-diphenyl methane diiso(thio)cyanate, naphtalene diiso(thio)cyanate, isophorone diiso(thio)cyanate, bis(iso(thio)cyanate methyl)cyclohexane, hexamethylene diiso(thio)cyanate and dicyclohexylmethane diiso(thio)cyanate.

There can be used a single polyiso(thio)cyanate monomer or a mixture thereof.

The addition of the polyiso(thio)cyanate monomer reduces gel time and improves the mechanical performance of the obtained resin.

When both a polythiol monomer and a polyiso(thio)cyanate monomer are present in the composition the weight ratio polyiso(thio)cyanate/polythiol is preferably equal to or less than 1.

The polymerizable compositions according to the invention may also include additives which are conventionally employed in polymerizable compositions intended for moulding optical articles, in particular ophthalmic lenses, in conventional proportions, namely inhibitors, dyes, UV absorbers, perfumes, doedorants, antioxidants, antiyellowing agents and release agents.

The perfumes allow the odour of the compositions to be masked, in particular during surfacing or outering operations.

In particular, usual UV absorbers such as those commercialized under the tradenames UV 5411®, UV 9®, Tinuvin 400® and Tinuvin 312® may be used in amounts generally up to 0.4% by weight of the total polymerizable monomers weight.

Also, the compositions of the invention preferably comprise a release agent in an amount up to 0.1% by weight of the total polymerizable monomers weight.

Among the release agents there may be cited mono and dialkyl phosphates, silicones, fluorinated hydrocarbon, fatty acids and ammoniumm salts. The preferred release agents are mono and dialkyl phosphates and mixtures thereof. Such release agents are disclosed inter alia in documents U.S. Pat. Nos. 4,662,376, 4,975,328 and EP-271.839.

The composition of the present invention can be easily polymerized by mixing the polymerizable monomers with the catalyst system at room temperature or under heat.

Preferably, polymerization is effected by moderate heating and most preferably using a two-step heating process comprising a first step in which the mixture is heated up to gelification at a first temperature of 50° C. or less, preferably at a temperature of 25° C. to 50° C., and thereafter in a second step is heated at a temperature higher than the first temperature, typically up to 90° C. to obtain a hard resin. Preferably, the second temperature ranges from 60 to 90° C. Polymerization process usually lasts for 6 hours or less, typically 3 hours or less. In the case of the two steps heating process, first step typically lasts for about 1 hour and second step lasts for about 2 hours.

In the following examples, unless otherwise stated, all parts and percentages are by weight.

EXAMPLES 1 AND 2 AND COMPARATIVE EXAMPLES C1 AND C2

Polymerizable compositions are prepared by mixing at room temperature the components indicated in Table I below. The compositions are poured into the mold cavity of typical two-part glass mould for making optical lenses of optical power −2.00 and −4.25. The compositions are then cured in an oven as indicated in Table I. Properties of the resulting lenses are also given in Table I.

TABLE I

|  | Ex. 1 | Ex. 2 | C1 | C2 |
|---|---|---|---|---|
|  | Parts by weight | | | |
| Formulation Polymerizable monomers | | | | |
| Bis(β-epithiopropyl)disulfide | 100 | — | 100 | 100 |
| Bis(β-epithiopropyl)sulfide | — | 100 | — | — |
| Catalytic system | | | | |
| N,N-dimethylcyclohexylamine | — | — | — | 0.02 |
| N,N-dicyclohexylmethylamine | 0.15 | 0.15 | 0.15 | 0.10 |
| KSCN solution* | 0.11 | 0.11 | — | — |

TABLE I-continued

|  | Ex. 1 | Ex. 2 | C1 | C2 |
|---|---|---|---|---|
|  | Parts by weight | | | |
| Polymerization cycle | Hours | | | |
| 45° C. | 1 | 1 | 1 | 1 |
| 80° C. | 2 | 2 | 2 | 2 |
| State of the composition after polymerization cycle | Hard resin | Hard resin | No gel | No gel |

EXAMPLE 3 AND COMPARATIVE EXAMPLES C3 AND C4

Optical lenses having optical powers of −2.00 and −4.25 dioptries are moulded as in examples 1 and 2, using the compositions and polymerization cycle indicated in Table II. Results are also given in Table II.

TABLE II

|  | Ex. 3 | C3 | C4 |
|---|---|---|---|
|  | Parts by weight | | |
| Formulation Polymerizable monomers | | | |
| Bis(β-epithiopropyl)sulfide | 90.0 | 90.0 | 90.0 |
| 1,2-bis(2'-mercaptoethylthio)-3-mercaptopropane | 10.0 | 10.0 | 10.0 |
| Catalyst system | | | |
| N,N-dicyclohexylmethylamine | 0.15 | 0.50 | — |
| KSCN solution* | 0.11 | — | 0.29 |
| Polymerization cycle | | | |
| 30° C./1 hour | Gel | No gel | No gel |
| 80° C./2 hours | Hard resin | Much striation | Runaway reaction |

As shown by example 3, the catalyst system of the invention is very effective to give a fast gel. The use of either a tertiary amine or KSCN solution alone does not give a good fast gel, even with increased catalyst concentration.

EXAMPLES 4 TO 8

Optical lenses having optical powers from −2.00 to −10.00 dioptries are moulded as previously described using the compositions and the polymerization cycles indicated in Table III.

TABLE III

|  | Ex. 4 | Ex. 5 | Ex. 6 | Ex. 7 | Ex. 8 |
|---|---|---|---|---|---|
|  | | | Parts by weight | | |
| Formulation | | | | | |
| Bis(β-epithiopropyl)disulfide | 85.0 | 85.0 | 90.0 | 90.0 | — |
| Bis(β-epithiopropyl)sulfide | — | — | — | — | 90.0 |
| Xylylene diisocyanate | 7.5 | 7.5 | — | — | — |
| 1,2-bis(2'-mercaptoethyl-thio)-3-mercaptopropane | — | 7.5 | — | 10.0 | 10.0 |
| Thiol A*** | 7.5 | — | — | — | — |
| 2-(2-sulfanylethylthio)-3-[3-sulfanyl-2-(2-sulfanylethyl-thio)propylthio]propane-1-thiol** | — | — | 10.0 | — | — |
| Catalyst system | | | | | |
| Dicyclohexylmethylamine | 0.15 | 0.15 | 0.15 | 0.15 | 0.15 |
| KSCN solution* | 0.08 | 0.08 | 0.24 | 0.11 | 0.11 |
| Polymerization cycle | | | Hours | | |
| 45° C. | 1 | 1 | 1 | 1 | 1 |
| 80° C. | 2 | 2 | 2 | 2 | 2 |
| State after polymerization cycle | Hard resin | Hard resin | Hard resin | Hard resin | Hard resin |
| Lens properties | | | | | |
| Striation | No | No | No | No | No |
| Haze | No | No | No | No | No |
| Demoulding | No | No | No | No | No |
| Surface defects | No | No | No | No | No |
| Softening temperature (° C.) | >80 | >80 | >80 | >80 | >80 |
| Yellowness index | 1.54 | — | — | 1.36 | — |
| Tinting (%) | 68.0 | — | — | 74 | — |
| Light transmission (%) | 90.0 | — | — | 90.1 | — |
| $n_D^{25}$ | 1.73 | — | — | 1.74 | — |
| Abbe number $\nu_D$ | 32 | — | — | 33 | — |

*KSCN solution: 8.49% KSCN/34.85% Crown ether (18-crown-6)/56.66% 2-mercaptoethanol
**Mixture of:

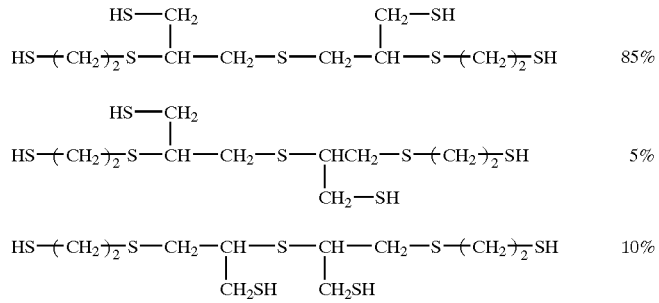

***Thiol A is a polythioprepolymer made by reacting xuylylene diisocyanate and 1,2 bis(2'-mercaptoethylthio)-3-mercaptopropane in a molar ratio 1/8.

Haze is determined by Arc lamp with naked eye.
Demoulding and surface defects are determined by naked eye to see if there is optical or cosmetic defects (lines, . . . ).
No demoulding means that there is no premature demoulding before the end of the polymerisation.
A premature demoulding implies that surface defects are created on the lens.
Yellow index (YI) is measured by Ultrascan of Hyperlab.
Tinting is conducted by dipping the lens in a BPI black dye solution at 94° C. for 45 minutes.
The value which is mentioned is the light transmission of the lens after tinting.
Light transmission is measured by Haze-Guard Plus of BYK Gardner.

EXAMPLE 9

Optical lenses are made as in the previous examples. Formulation, cure cycle and lens performances are given in the table below.

|  | Parts by weight |
|---|---|
| Formulation | |
| bis(β-epithiopropyl)disulfide | 89.0 |
| XDI | 1.0 |
| Polythio prepolymer**** | 10.0 |
| Dicyclohexylamine | 0.60 |

-continued

| | Parts by weight |
|---|---|
| KSCN solution* | 0.10% |
| Cure cycle | |
| 20 C. | 20 min (gel) |
| 80 C. | 2 hr (post cure) |
| State after cure cycle | Hard resin |
| Lens Performance | |
| Striation | No |
| Haze | No |
| De-moulding | No |
| Surface defect | No |
| Softenning temperature | >80 C. |
| Yellowness index | 1.48 |
| Tinting | 71 |
| Light transmission | 90.0 |
| Refractive index ($n_D^{25}$) | 1.74 |
| Abbe number $v_D$ | 33 |

****Polythioprepolymer is a polythiol prepolymer made by mixing and polymerising 2-(2-sulfanylethylthio)-3-[3-sulfanyl-2-(2-sulfanylethyl-thio)propylthio]propane-1-thiol and bis(β-epithiopropyl)disulfide (80/20 weight ratio).

We claim:

1. Polymerizable composition for making episulfide based resins comprising:
   A) at least one episulfide compound bearing at least one episulfide and at least one functional group capable of polymerizing with episulfide groups, and
   B) an effective amount of a polymerization catalyst system comprising:
   at least one salt of formula $$M_m^{p+} Y_n^-$$

wherein
   $M^{p+}$ is a cation selected from the group consisting of alkaline metals, alkaline earth metals, transitions metals and ammonium groups of formula $NR^+_4$ in which R is an alkyl radical,
   $Y^-$ is an anion such as the corresponding acid YH has a pKa fulfilling the condition $0.5 \leq pKa \leq 14$ with the proviso that when $M^{p+}$ is an ammonium group, the catalyst system further comprises an electro-donor compound,
   P is the valency of the cation,
   $n = m \times p$, and
   at least one tertiary amine.

2. Polymerizable composition according to claim 1, wherein the associated acid YH has a pKa fulfilling the condition $0.5 \leq pKa \leq 8$.

3. Polymerizable composition according to claim 1, wherein $Y^-$ is selected from the group consisting of thiocyanate, carboxylate, thiocarboxylate, $RS^-$ wherein R is an alkyl group or phenyl group, acetylacetonate, diketone, acetoacetic ester, malonic ester, cyanoacetic ester, and ketonitrile.

4. Polymerizable composition according to claim 1, wherein the cation $M^{p+}$ is selected from the group consisting of $Li^+$, $Na^+$, $K^+$, $Rb^+$, $Mg^{2+}$, $Ca^{2+}$, $Ba^{2+}$ and $Al^{3+}$.

5. Polymerizable composition according to claim 1, wherein the salt is KSCN.

6. Polymerizable composition according to claim 1, wherein the salt is present in amount of 0.001 to 2.5%, based on the total weight of the polymerizable monomers present in the composition.

7. Polymerizable composition according to claim 6, wherein the salt is present in an amount of 0.001 to 1% based on the total weight of the polymerizable monomers present in the composition.

8. Polymerizable composition according to claim 1, wherein the tertiary amine has formula:

$(R)_3N$ in which the R groups represent, independently from each other, an alkyl radical, a cycloalkyl radical or mixtures thereof.

9. Polymerizable composition according to claim 1, wherein the at least one tertiary amine is selected from N,N-dimethylcyclohexylamine, N,N-dicyclohexylethylamine or mixtures thereof.

10. Polymerizable composition according to claim 1, wherein the tertiary amine is present in the composition from 0.05 to 5%, based to the total weight of the polymerizable monomers present in the composition.

11. Polymerizable composition according to claim 10, wherein the tertiary amine is present from 0.05 to 2%.

12. Polymerizable composition according to claim 1, further comprising an electro-donor compound enhancing the reactivity of the polymerization reaction.

13. Composition according to claim 12, wherein the electrodonor compound is selected from the group consisting of acetonitrile compounds, amide compounds, sulfones and sulfoxides, trialkylphosphites, nitro compounds, ethyleneglycol ethers, crown ethers and kryptates.

14. Composition according to claim 13, wherein the crown ethers and the kryptates are selected from the compounds of formulae:

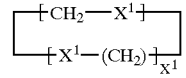

or

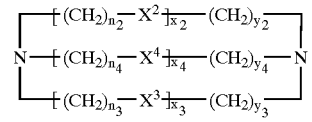

wherein $X^1$ represents O, S or NH, $x_1$ is an integer from 3 to 6,
$X^2$, $X^3$ and $X^4$ represent O or S,
$n_2$, $n_3$, $n_4$, $y_2$, $y_3$, $y_4$ are 2 or 3, and
$x_2$, $x_3$, $x_4$ are 2 or 3.

15. Composition according to claim 13, wherein the electro-donor compound represents up to 5% by weight of the total weight of the polymerizable monomers present in the composition.

16. The composition of claim 1, wherein the episulfide monomer comprises one or more episulfide structure of formula:

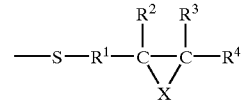

in which $R^1$ represents a hydrocarbon group having 1 to 10 carbon atoms, $R^2$, $R^3$ and $R^4$ each represents an hydrogen atom or a hydrocarbon group having 1 to 10 carbon atoms, X represents S or O with the provisio that in the molecule the average number of S represented by X is about 50% of the total number of S and O constituting the three membered ring.

17. Composition of claim 1, wherein the episulfide monomer is a compound of formula:

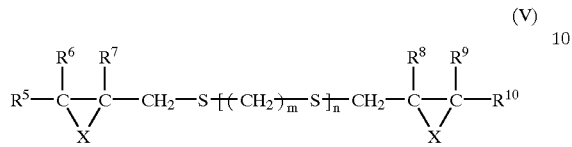

(V)

in which $R^5$, $R^6$, $R^7$, $R^8$, $R^9$ and $R^{10}$ each represents an hydrogen atom or a hydrocarbon group having 1 to 10 carbon atoms, X represents S or O with the proviso that, in the molecule, the average number of S represented by X is about 50% or more of the total number of S and O constituting the three member rings, m represents an integer from 0 to 6 and n represents an integer from 0 to 4.

18. The composition of claim 17, wherein X is S.

19. The composition of claim 1, wherein the polymerizable monomers comprise solely episulfide monomers.

20. The composition according to claim 1, further comprising one or more polythiols of formula:

$R'(SH)_{n'}$ in which n' is an integer from 2 to 6 and R' is an organic group of valency equal to n'.

21. The composition according to claim 20, wherein the polythiol represents 0 to 30% by weight of the total weight of the polymerizable monomers present in the composition.

22. Composition according to claim 1, further comprising one or more polyiso(thio)cyanate monomers.

23. Composition according to claim 22, wherein the polyiso(thio)cyanate monomers are selected from the compounds having the formulae:

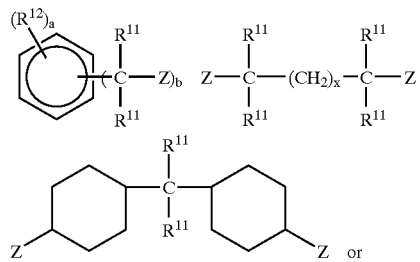

-continued

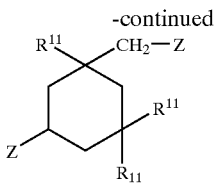

wherein:
$R^{11}$ is independently H or $C_1$-$C_5$ alkyl group,
$R^{12}$ is H, an halogen, or a $C_1$-$C_5$ alkyl group,
Z is —N=C=O or —N=C=S;
a is an integer ranging from 1 to 4, b is an integer ranging from 2 to 4 and a+b≦6; and
x is an integer from 1 to 10.

24. Composition according to claim 23, wherein the polyiso(thio)cyanate monomers are selected from the group consisting of tolylene diiso(thio)cyanate, phenylene diiso(thio)cyanate, ethylphenylene diiso(thio)cyanate, isopropyl phenylene diiso(thio)cyanate, dimethylphenylene diiso(thio)cyanate, diethylphenylene diiso(thio)cyanate, diisopropylphenylene diiso(thio)cyanate, trimethylbenzyl triiso(thio)cyanate, xylylene diiso(thio)cyanate, benzyl triiso(thio)cyanate, 4,4'-diphenyl methane diiso(thio)cyanate, naphtalene diiso(thio)cyanate, isophorone diiso(thio)cyanate, bis(iso(thio)cyanate methyl) cyclohexane, hexamethylene diiso(thio)cyanate and dicyclohexylmethane diiso(thio)cyanate and mixtures thereof.

25. Composition according to claim 22, wherein the polyiso(thio)cyanate monomer or the mixture thereof represents up to 30% by weight of the total weight of the polymerizable monomers present in the composition.

26. Process for making a cast episulfide based resin article comprising:
preparing a composition as set forth in claim 1;
filling a mold with the prepared composition;
heating the filled mold at a first temperature of 50° C. or less up to the obtention of a gel;
thereafter, heating at a second temperature higher than the first temperature up to the obtention of a hard resin; and
removing the cast article from the mold.

27. The process according to claim 26, wherein the first temperature ranges from 20° C. to 50° C.

28. The process according to claim 26, wherein the second temperature ranges from 60 to 90° C.

29. The process according to claim 26, wherein heating at the first temperature lasts for 15 minutes to about 1 hour and heating at the second temperature lasts for about 2 hours.

30. The process according to claim 26, wherein the cast article is an optical article.

* * * * *

UNITED STATES PATENT AND TRADEMARK OFFICE
CERTIFICATE OF CORRECTION

PATENT NO. : 6,891,017 B2
DATED : May 10, 2005
INVENTOR(S) : Jiang et al.

It is certified that error appears in the above-identified patent and that said Letters Patent is hereby corrected as shown below:

Title page,
Item [73], Assignee, please delete "General" and insert -- Generale --.

Column 13,
Line 51, please delete "associated" and insert -- corresponding --.

Column 14,
Line 13, please delete "selected from".
Line 31, please delete "selected from the".

Column 15,
Lines 41 and 42, please delete "monomers are selected from the compounds" and insert -- monomer is a compound --.

Signed and Sealed this

Eighteenth Day of October, 2005

JON W. DUDAS
*Director of the United States Patent and Trademark Office*

UNITED STATES PATENT AND TRADEMARK OFFICE
CERTIFICATE OF CORRECTION

PATENT NO.     : 6,891,017 B2
DATED          : May 10, 2005
INVENTOR(S)    : Jiang et al.

It is certified that error appears in the above-identified patent and that said Letters Patent is hereby corrected as shown below:

Title page,
Item [73], Assignee, please delete "General" and insert -- Generale --.

Column 13,
Line 51, please delete "associated" and insert -- corresponding --.

Column 14,
Line 13, please delete "selected from".
Line 31, please delete "selected from the".

Column 15,
Lines 41 and 42, please delete "monomers are selected from the compounds" and insert -- monomer is a compound --.

Signed and Sealed this

First Day of November, 2005

JON W. DUDAS
*Director of the United States Patent and Trademark Office*